United States Patent
van Groeningen et al.

(10) Patent No.: US 7,162,300 B2
(45) Date of Patent: Jan. 9, 2007

(54) SYNCHRONIZED ATRIAL ANTI-TACHY PACING SYSTEM AND METHOD

(75) Inventors: Chritianus J. J. E. van Groeningen, Utrecht (NL); Joanneke Gerrigje Groen, Velp (NL); Malcom J. Begemann, Velp (NL)

(73) Assignee: Medtronic, Inc., Minneapolis, MN (US)

( * ) Notice: Subject to any disclaimer, the term of this patent is extended or adjusted under 35 U.S.C. 154(b) by 571 days.

(21) Appl. No.: 10/435,071

(22) Filed: May 12, 2003

(65) Prior Publication Data

US 2004/0138715 A1 Jul. 15, 2004

Related U.S. Application Data

(60) Provisional application No. 60/439,460, filed on Jan. 13, 2003.

(51) Int. Cl.
*A61N 1/362* (2006.01)
(52) U.S. Cl. .......................................................... 607/14
(58) Field of Classification Search .................... 607/9, 607/11–16; 600/510
See application file for complete search history.

(56) References Cited

U.S. PATENT DOCUMENTS

| | | | |
|---|---|---|---|
| 4,280,502 A | 7/1981 | Baker, Jr. et al. | |
| 4,316,472 A | 2/1982 | Mirowski et al. | |
| 4,375,817 A | 3/1983 | Engle et al. | |
| 4,379,459 A | 4/1983 | Stein | |
| 4,384,585 A | 5/1983 | Zipes | |
| 4,390,021 A | 6/1983 | Spurrell et al. | |
| 4,398,536 A | 8/1983 | Nappholz et al. | |
| 4,406,287 A | 9/1983 | Nappholz et al. | |
| 4,408,606 A | 10/1983 | Spurrell et al. | |
| 4,466,063 A | 8/1984 | Segarra et al. | |

(Continued)

FOREIGN PATENT DOCUMENTS

EP     0 436 517 A2     7/1991

(Continued)

OTHER PUBLICATIONS

Fearnot et al. *A Review of Pacemakers That Physiologically Increase Rate: The DDD and Rate-Responsive Peacemakers*, Progress In Cardiovascular Diseases, Sep./Oct. 1986, pp. 145-164, vol. XXIX No. 2, Purdue University, Indiana, USA.

(Continued)

*Primary Examiner*—George Manuel
(74) *Attorney, Agent, or Firm*—Michael C. Soldner; Girma Wolde-Michael

(57) ABSTRACT

A system and method for an implantable cardiac pacing device provide for delivery of anti-tachycardia pacing of the atrium upon detection of atrial tachycardia combined with automatic re-synchronization of ventricular pacing directly following the last atrial pulse of the anti-tachycardia scheme. At the onset of delivery of the ATP train or like scheme of ATP, an appropriate ventricular pacing interval is calculated to enable asynchronous pacing of the ventricle during the ATP and synchronous delivery of the next ventricular pulse at a delay following the end of the ATP train. Upon determination of AT, an algorithm is used to calculate if a ventricular pacing interval can be found that meets maximum and minimum pacing criteria and also provides that the next ventricular pace pulse following the end of the ATP train will follow the last atrial pulse of the train by a suitable AV delay. If such a suitable pacing interval is found, the ventricular pacing interval is set to a temporary value and the train is delivered. If such a pacing interval cannot be initially determined the system waits for one more atrial sense and then repeats the determination to find such a suitable ventricular pacing interval.

36 Claims, 8 Drawing Sheets

U.S. PATENT DOCUMENTS

| | | |
|---|---|---|
| 4,467,810 A | 8/1984 | Vollmann |
| 4,476,868 A | 10/1984 | Thompson |
| 4,566,063 A | 1/1986 | Zolnowsky et al. |
| 4,574,437 A | 3/1986 | Segerstad et al. |
| 4,577,633 A | 3/1986 | Berkovits et al. |
| 4,587,970 A | 5/1986 | Holley et al. |
| 4,593,695 A | 6/1986 | Wittkampf |
| 4,726,380 A | 2/1988 | Vollmann et al. |
| 4,727,877 A | 3/1988 | Kallok |
| 4,800,883 A | 1/1989 | Winstrom |
| 4,821,723 A | 4/1989 | Baker, Jr. et al. |
| 4,830,006 A | 5/1989 | Haluska et al. |
| 4,880,005 A | 11/1989 | Pless et al. |
| 4,941,471 A | 7/1990 | Mehra |
| 4,949,719 A | 8/1990 | Pless et al. |
| 4,953,551 A | 9/1990 | Mehra |
| 5,099,838 A | 3/1992 | Bardy |
| 5,117,824 A | 6/1992 | Keimel et al. |
| 5,131,388 A | 7/1992 | Pless et al. |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,193,550 A * | 3/1993 | Duffin ................ 600/510 |
| 5,199,428 A | 4/1993 | Obel et al. |
| 5,207,218 A | 5/1993 | Carpentier et al. |
| 5,269,298 A | 12/1993 | Adams et al. |
| 5,311,388 A | 5/1994 | McLaren |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,545,186 A | 8/1996 | Olson et al. |
| 5,690,686 A | 11/1997 | Min et al. |
| 5,800,465 A | 9/1998 | Thompson et al. |
| 5,928,271 A * | 7/1999 | Hess et al. ................ 607/14 |
| 6,029,087 A | 2/2000 | Wohlgemuth |
| 6,091,991 A | 7/2000 | Warren |
| 6,115,632 A * | 9/2000 | Akers et al. .............. 607/9 |
| 6,128,352 A | 10/2000 | Maeda |
| 6,128,532 A | 10/2000 | Stoop et al. |
| 2001/0014816 A1 | 8/2001 | Hsu et al. |

FOREIGN PATENT DOCUMENTS

| | | |
|---|---|---|
| WO | WO 92/18198 | 10/1992 |
| WO | WO92/18198 | 10/1992 |

OTHER PUBLICATIONS

Olson et al. *Onset and Stability for Ventricular Tachyarrhythmia Detection in an Implantable Pacer—Cardioverter-Defibrillator*, Computers in Cardiology, Oct. 7-10, 1986, pp. 167-170, IEEE Computer Society Press.

Arzbaecher et al. *Automatic Tachycardia Recognition*, PACE, May-Jun. 1984, pp. 541-547.

Arzbaecher, et al., "Automatic Tachycardia Recognition", *PACE*, vol. 7, May-Jun. 1984, Part II, pp. 541-547.

Fearnot, et al., "A Review of Pacemakers That Physiologically Increase Rate: The DDD and Rate-Responsive Pacemakers", Progress in Cardiovascular Diseases, vol. XXIX, No. 2, Sep.-Oct. 1986, pp. 145-164.

Olson, et al., "Onset and Stability for Ventricular Tachyarrhythmia Detection in an Implantable Pacer-Carioverter-Defibrillator", *Computers in Cardiology—IEEE Computer Society Press*, Oct. 7-10, 1986, pp. 167-170.

\* cited by examiner

SYNCHRONIZED ATRIAL ANTI-TACHY PACING SYSTEM AND METHOD

This application claims priority to provisional U.S. Application No. 60/439,460 filed 13 Jan. 2003.

FIELD OF THE INVENTION

This invention relates to implantable cardiac pacing devices that incorporate atrial anti-tachycardia control, and in particular dual chamber pacing devices with atrial anti-tachy control that optimize synchronous ventricular pacing.

BACKGROUND OF THE INVENTION

Modern implantable cardiac pacing devices are designed for efficient dual or multiple chamber pacing as well as detection and treatment of dangerous cardiac arrhythmias. A dual chamber pacing device provides the capability of synchronous pacing, whereby the ventricle is paced in synchrony with the just preceding atrial beat (intrinsic or paced), thereby approximating the normal healthy coordination between the atrium and the ventricle and thus optimizing cardiac output. However, if the atrium is seized with an arrhythmia, such synchronous pacing cannot be resumed until after the arrhythmia abates or is somehow reverted. In the case of atrial tachycardia (AT), a malignant arrhythmia, pacemakers can respond with normally effective atrial pacing schemes to arrest or stop the AT, after which the pacemaker can resume synchronous pacing when the cardiac condition is stabilized. The problem is that the atrium remains vulnerable to a recurring episode of tachycardia following AT treatment, particularly if the two chambers are not operating in an efficient synchronous manner. What is important, then, and a main feature of this invention, is enabling the pacemaker or other implantable device (ipg) to resume such synchronous pacing as quickly as possible after the conclusion of the AT response.

The advantage of synchronous pacing is well established. For a patient at rest, AV synchrony improves cardiac output by about 20–25%; the improvement decreases with exercise. The intrinsic atrial rate, however, is not always reliable for control of ventricular pacing. Pacemaker patients are, by definition, in a class that is subject to cardiac abnormalities. In particular, AT is a concern, and the pacemaker or ipg must be able to detect AT and provide an appropriate response to terminate the AT. As used here, AT means an abnormally high atrial rate, e.g., a rate of intrinsic atrial beats above 120–150 bpm. The definition of AT may be programmed into the device by a physician, and may be set at a value within a range of, for example, 100–180 bpm. Most pacing devices have a programmable upper rate limit above which the ventricle will not be paced, and this limit may serve to define tachy senses. In a typical arrangement, when such high rate tachy senses occur consecutively or in predominance over a given time period, AT is recognized and an anti-tachy pacing (ATP) mode automatically takes over to stop the AT.

There are many different ATP schemes illustrated in the patent art. Table 1 below lists representative patent and literature references that show different forms of ATP.

TABLE 1

| Patent/Doc. No. | Inventor(s) | Issue/Pub Date |
| --- | --- | --- |
| 4,280,502 | Baker, Jr. et al. | Jul. 28, 1981 |
| 4,390,021 | Spurrell et al. | Jun. 28, 1983 |

TABLE 1-continued

| Patent/Doc. No. | Inventor(s) | Issue/Pub Date |
| --- | --- | --- |
| 4,398,536 | Nappholz et al. | Aug. 16, 1983 |
| 4,406,287 | Nappholz et al. | Sep. 27, 1983 |
| 4,408,606 | Spurrell et al. | Oct. 11, 1983 |
| 4,467,810 | Vollmann | Aug. 28, 1984 |
| 4,574,437 | Segerstad et al. | Mar. 11, 1986 |
| 4,577,633 | Berkovitz et al. | Mar. 25, 1986 |
| 4,587,970 | Holly et al. | May 13, 1986 |
| 4,593,695 | Wittkampf | Jun. 10, 1986 |
| 4,491,471 | Mehra | Jul. 17, 1990 |

All patents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

A common form of ATP is to deliver a train of pulses to the atrium immediately after AT is declared. In delivering an ATP train, or burst, different sequences of atrial pulses can be used, with the timing being adjusted for maximum interruption of the tachycardia. Atrial tachycardia is thought to be characterized by a re-entry feedback loop in the atrium, whereby each atrial conduction induces another beat before the natural pacemaker triggers the next normal beat. The timing of the feedback conduction can be variable, such that it is difficult to determine the best time to deliver a reverting pulse that can interrupt the arrhythmia. The basic idea of the train is to deliver a series of pulses before the next tachy occurrence, to enhance the possibility of interruption. It is thought that each successive pulse of the sequence enlarges the area of the atrium that is conditioned to respond to a pacing pulse, such that by the end of the train the entire atrium is in condition to be captured by an atrial pulse (AP). The sequence, whether called a train or burst or whatever, can be programmed for each patient, and may even vary based on history. As used herein, ATP refers to any sequence of atrial pulses delivered for the purpose of interrupting atrial tachycardia or like arrhythmias. However, the various ATP trains have in common the features that atrial sensing is abolished while the ATP pulses are being delivered, and once the train is started the order and timing of the ATP pulses is set, i.e., the train is irrevocable.

As stated above, it is important to continue with synchronous pacing as soon as possible after an AT episode. In fact, establishing synchronous pacing quickly after an abnormal episode is crucial, due to the possibility of mediating or permitting re-establishment of the tachycardia. By way of example, following a premature atrial contraction (PAC) it is known to deliver an atrial sync pulse (ASP) that is timed to enable the pacer to re-establish snychrony with the next delivered ventricular pulse. This is done in order to prevent pacemaker mediated tachycardia. Likewise, following an AT episode, there is a danger of a new AT episode if the next ventricular pace pulse is not synchronized to the last atrial pulse of the ATP. An asynchronous ventricular pulse could put stress on the atrium, which increases the vulnerability to AT or AF. Or, such an asynchronous pulse could lead to retrograde conduction back to the atrium which could induce AT or AF. Moreover, these two mechanisms could stimulate the localized source of polarization that gave rise to the AT or AF in the first place. Thus, while the ATP has presumably stopped the feedback mechanism in the atrium that was admitting the AT, the atrium remains vulnerable following AT and a following asynchronous ventricular pulse can cause either electrical or mechanical interference capable of destabilizing the atrial tissue. This presents a serious problem that has not been addressed by the pacemaker art.

BRIEF SUMMARY OF THE INVENTION

It is an object of the invention to provide an implantable pacing device, and method of operation, that can sense and respond to atrial tachycardias, deliver an ATP train of atrial pulses, and deliver the next ventricular pulse in synchrony with the last atrial pulse of the train.

It is another object of the invention to provide an implantable pacing system capable of detecting a high rate atrial arrhythmia and responding to such arrhythmia with a fixed sequence of atrial pulses designed to revert the arrhythmia, and to deliver the very next ventricular pacing pulse that is due following the sequence in synchrony with the last atrial pulse of such sequence.

It is another object of the invention to provide a method of responding to a sensed atrial tachycardia or the like by delivering a planned ATP scheme of atrial pulses while delivering ventricular pulses without interruption and regaining synchronous ventricular pacing directly after such delivery.

In accord with the above objectives, there is provided a pacing system and method adapted for an implanted cardiac device, whereby an atrial anti-tachy pacing sequence is delivered to the patient's atrium upon sensing of AT, and where the next ventricular beat that follows the ATP is synchronized to the last atrial beat of the sequence. When AT is declared by the system, timing of an ATP is initiated referenced to the atrial sense (AS). At the same time, the pacing system determines whether the first ventricular pacing pulse after the end of the sequence can be delivered at the current ventricular pacing interval (PI) with an acceptable AV interval. If so, the ventricular pacing interval is not changed. If not, then the pacing system determines whether PI can be adapted to a value within predetermined maximum and minimum criteria in order to provide a ventricular pacing pulse with an acceptable AV interval following the last atrial pulse of the sequence. If so, the PI is lengthened or shortened appropriately. Upon determination of an acceptable ventricular PI, one or more ventricular pacing pulses may be delivered asynchronously during the duration of the ATP sequence, and the first ventricular pacing pulse after the end of the ATP train is delivered at an acceptable AV delay following the last atrial pulse of the sequence. In the event that the ventricular PI cannot be so adapted for synchrony when the determinations are first made, the system waits for the next atrial sense, determines a workable PI, and then delivers the ATP train and adapts ventricular PI appropriately.

In carrying out the method of the invention, the ATP sequence is delivered followed by a ventricular pacing pulse that is synchronized to the last atrial pulse. The prior ventricular PI is then restored, and the device determines whether the atrial rhythm is a normal sinus rhythm, i.e., whether AT has been reverted. If AT is again detected, the device repeats delivery of the ATP in the same manner until sinus rhythm is detected, again adapting ventricular PI in order to synchronize the ventricular pulse following the ATP sequence. Ventricular pacing is not interrupted, since one or more ventricular pace pulses, depending on the length of the ATP sequence, will be delivered asynchronously during the ATP sequence. But as soon as the ATP sequence is finished, and a normal sinus rhythm hopefully restored, ventricular pacing is immediately restored in a synchronous mode.

DETAILED DESCRIPTION OF THE INVENTION

Figure 1:
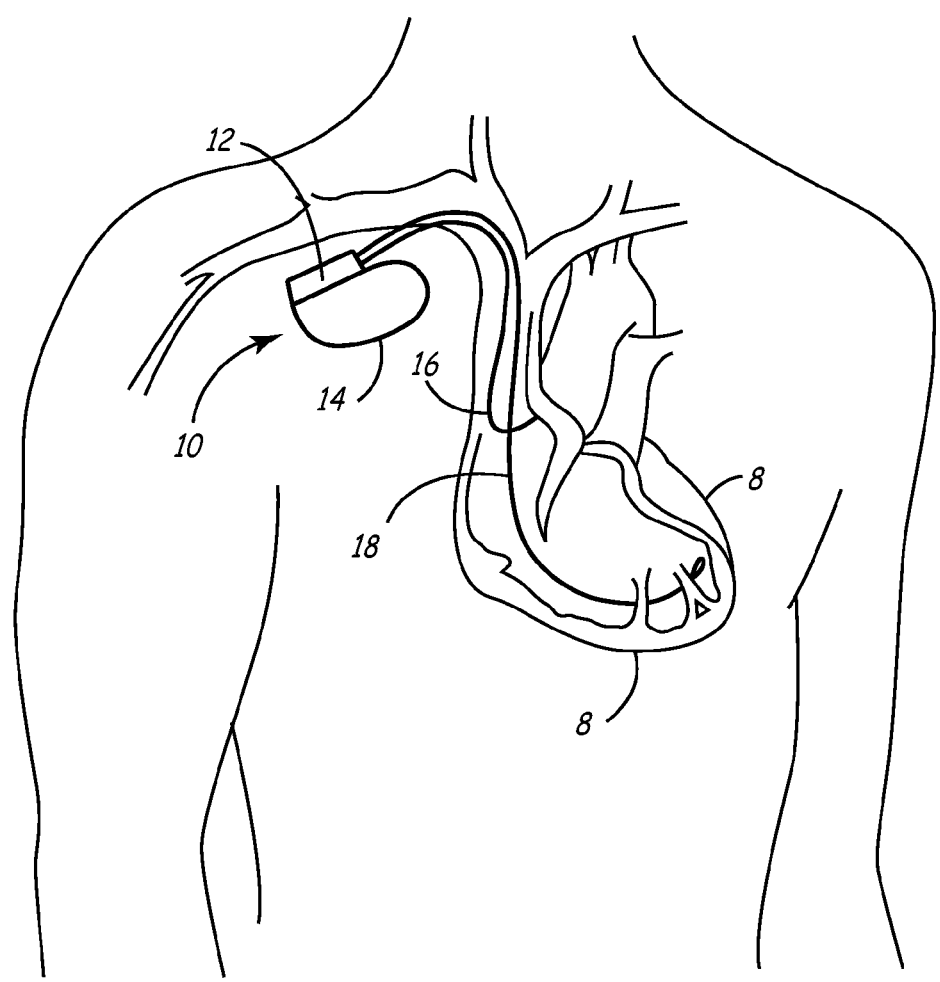
FIG. 1 is a simplified schematic view of one embodiment of an implantable medical device that can be employed in the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
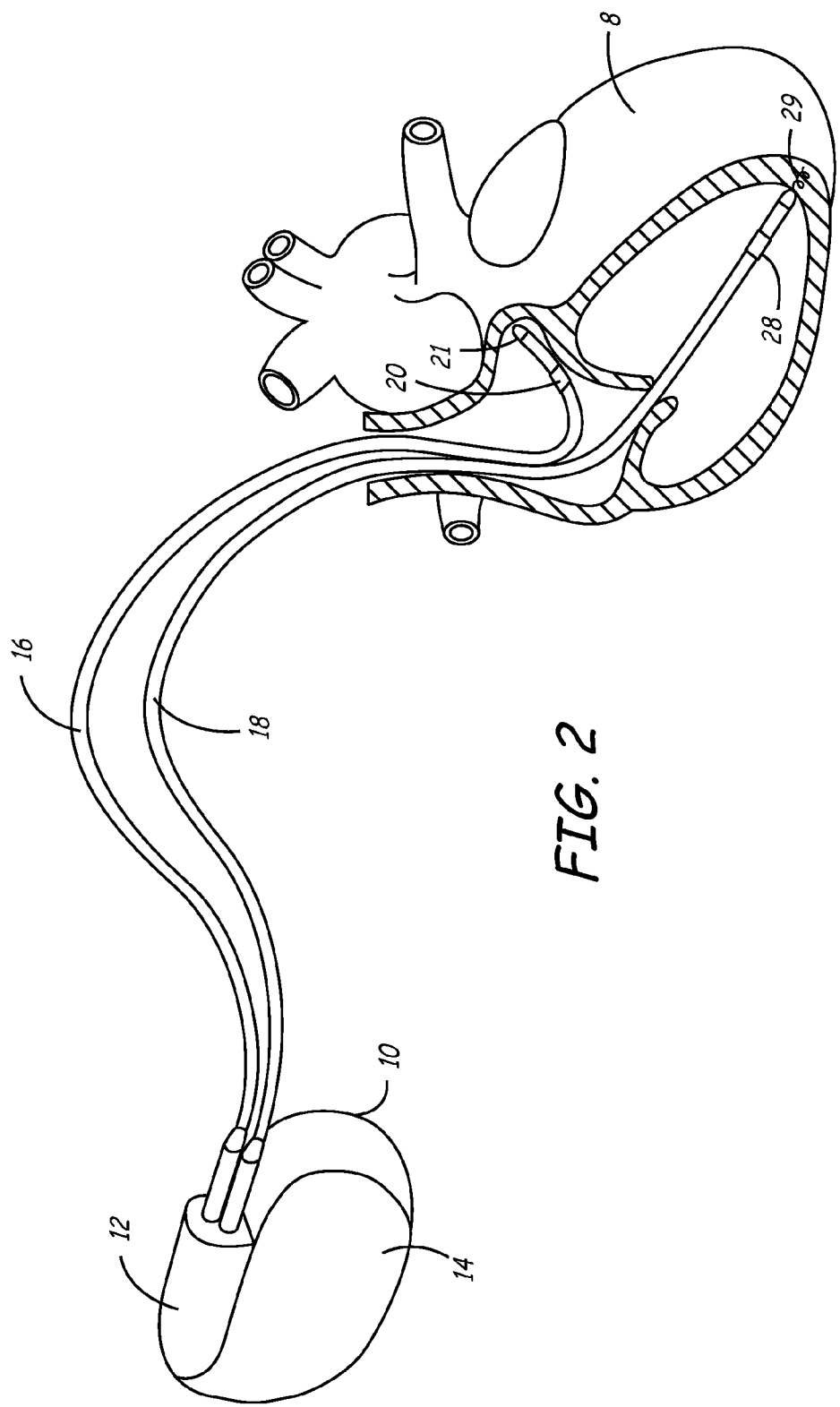
FIG. 2 is a graphic representation of an implantable medical device interconnected with a human or mammalian heart, illustrating the device connector portion and the leads between the device and the heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
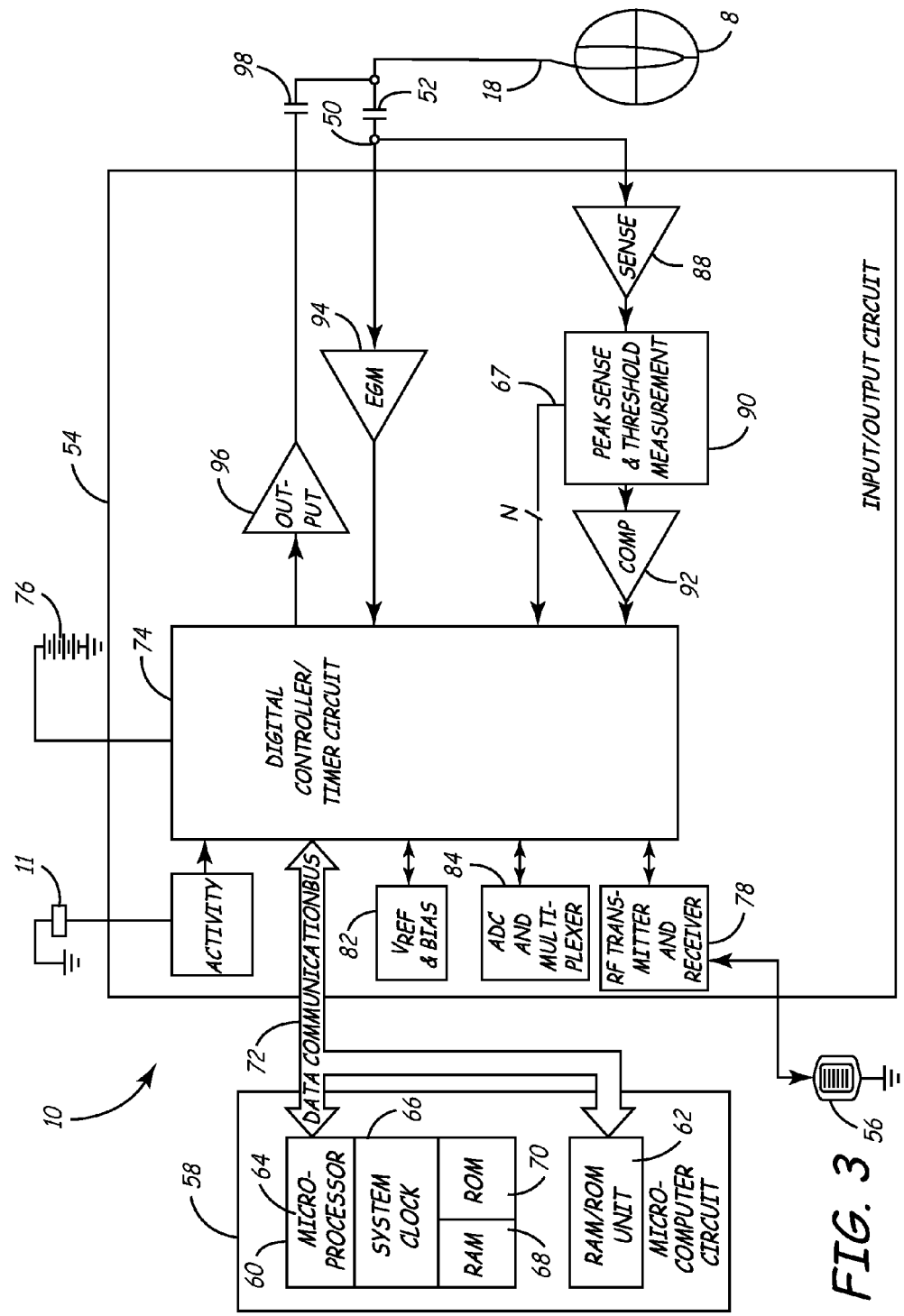
FIG. 3 is a functional schematic diagram showing the primary constituent components of an implantable medical device in accordance with an embodiment of this invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
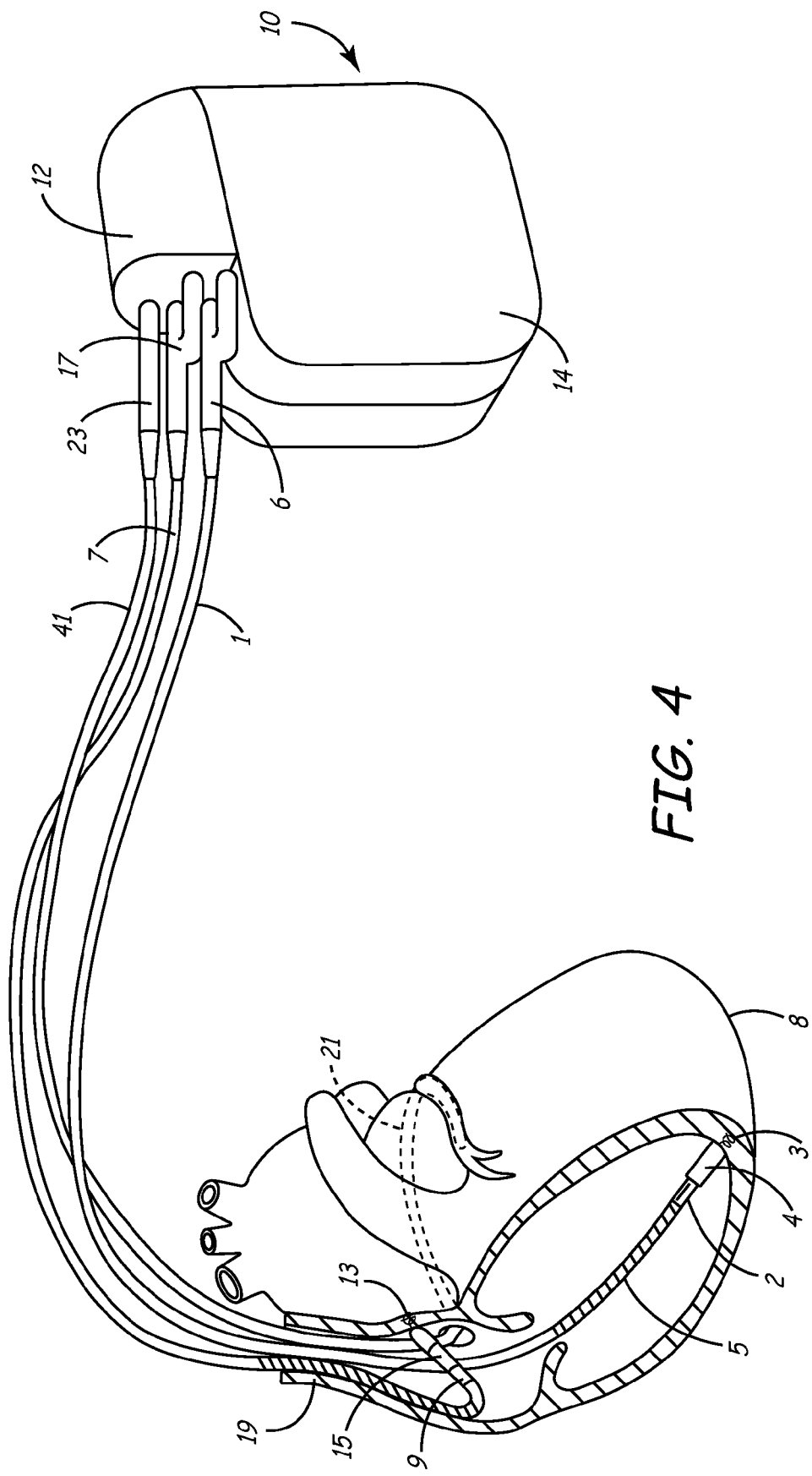
FIG. 4 is a graphic representation of an embodiment of this invention showing an implantable PCD device interconnected with a heart, the system of this embodiment providing pacing, cardio version and defibrillation.
Figure 5:
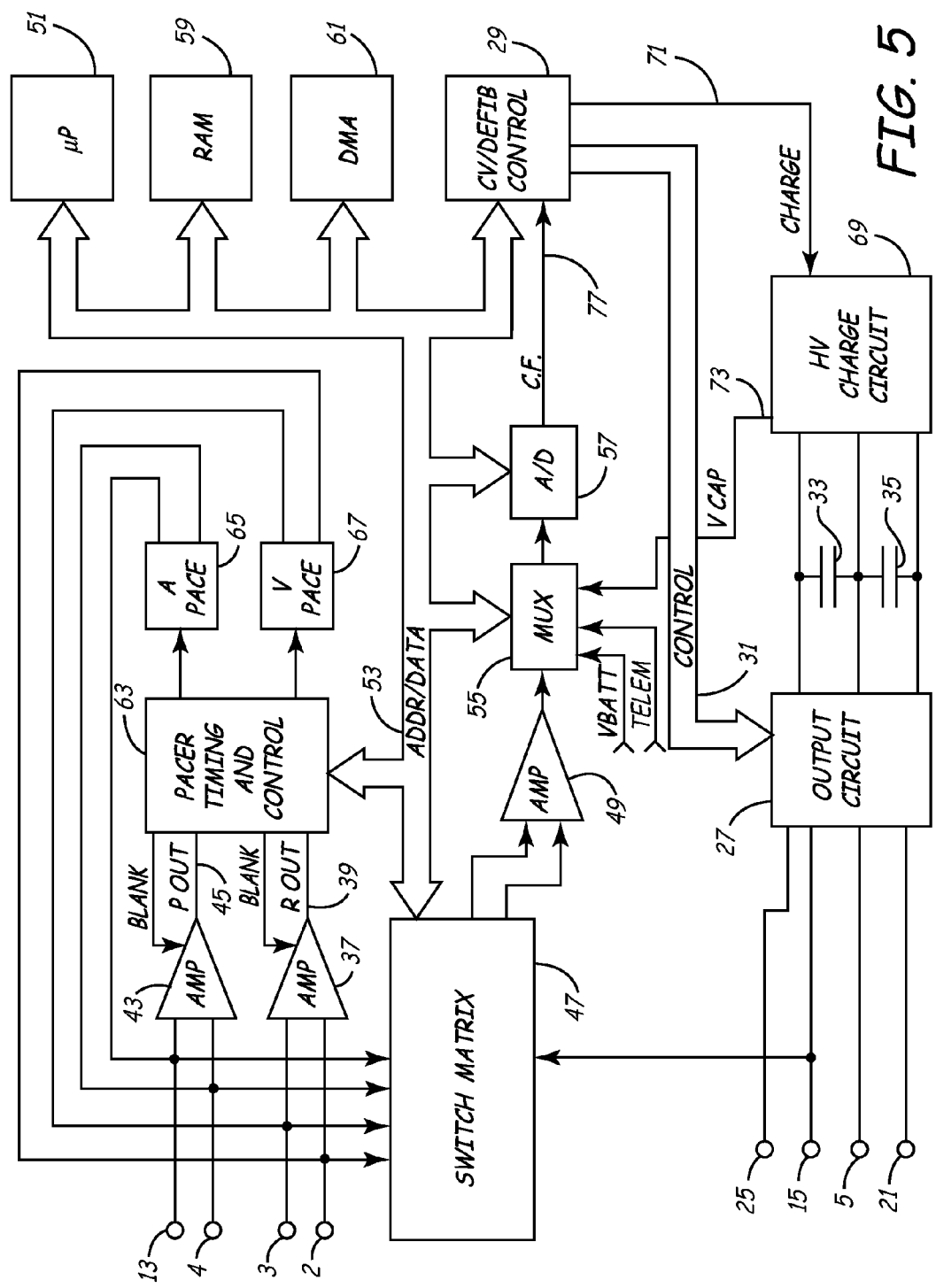
FIG. 5 is a functional schematic diagram of an implantable PCD embodiment of this invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations. IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

As used in this specification and the appended claims, the term "ATP train" refers to a sequence of pulses delivered to the patient's atrium for the purpose of interrupting, or stopping a detected episode of atrial tachycardia. Techniques of detecting AT and delivering ATP trains are well known in the art, as discussed above.

The algorithm used to provide for AV synchrony following an ATP train can be understood with reference to the timing diagram of FIG. 6A, and the following definitions in the table below.

TABLE 2

| Term | Definition |
| --- | --- |
| ATP interval (duration between pulses of the train) | y seconds |
| ATP train$_d$ | total duration of an ATP train (nominally n * y, where the train has n intervals) |
| Pacing Interval | the current ventricular cycle length |
| Minimum pacing interval | the minimum allowed cycle length to obtain resynchronization |
| Maximum pacing interval | the maximum allowed cycle length to obtain resynchronization |
| AV_min | the minimum allowed AV delay |
| AV_max | the maximum allowed AV delay |
| V_ATPi | the interval between the last ventricular event and the atrial tachy sense i |
| X | round up [(V_ATPi + ATP train$_d$ + AV_min)/Pacing Interval], where any fractional value is rounded up to the next integer |

Figure 6A:
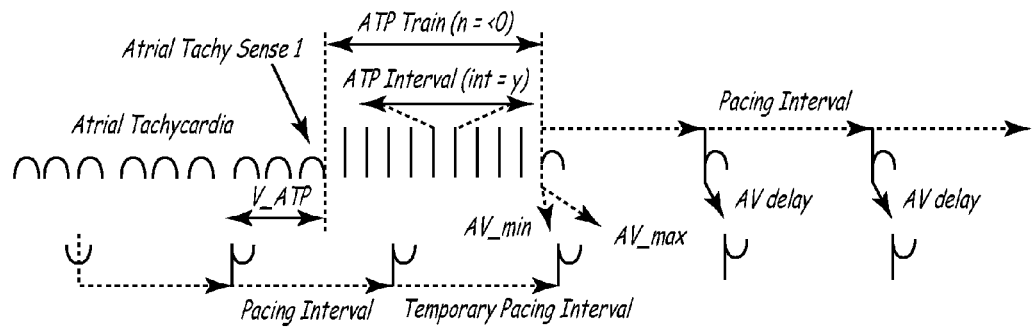
FIG. 6A is a timing diagram illustrating an ATP sequence and ventricular pacing with an unchanged ventricular pacing interval.

FIG. 6A illustrates a series of high rate atrial senses, with ventricular pace pulses being delivered at a certain pacing interval. In a conventional detection algorithm, AT is deemed to be sensed when a given number of senses occur at a rate above a tachy thershold and continue over a given duration of senses or time. As illustrated, AT is declared at Atrial Tachy Sense i, which occurs V_ATPi after the last ventricular pace pulse. In this situation if the temporary PI is maintained as the current PI, a ventricular pace pulse would be scheduled for delivery following the last pulse of the ATP train by more than AV_min but less than AV_max. Any ventricular pulse delivered within this timeframe would be properly synchronized, as seen in FIG. 6A. Thus, the first step of the sync algorithm is to determine if this condition is met: IF (X*pacing interval−V_ATPi) is <=(ATP Train$_d$+ AV_max), then deliver the ATP train and set the temporary (adapted) pacing interval to Pacing Interval (the current PI). This will achieve re-synchronization since the next VP will fall between AV_min and AV_max after the end of the train. In this situation, then, the PI remains unchanged.

Figure 6B:
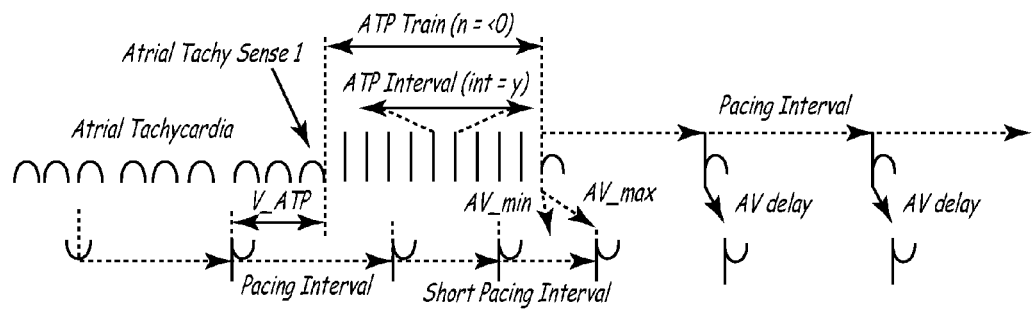
FIG. 6B is a timing diagram illustrating an ATP sequence and ventricular pacing with a shortened ventricular pacing interval.

If the above condition is not met, then it must be determined whether the ATP train can be delivered along with an adapted pacing interval that will permit the desired synchronous pacing after the end of the ATP train. FIG. 6B illustrates a Short Pacing Interval, and FIG. 6C illustrates a Long Pacing Interval, as determined in accord with this invention.

The logic is:

```
ELSE,
    Check if an ATP train can be delivered with an adapted Pacing Interval.
        Short Pacing Interval = (V_ATPi +ATP train_d+AV_max) / X
        Long Pacing Interval = (V_ATPi + ATP train_d - AV_min) / (X -1)
    IF (Short Pacing Interval >= Mininum Pacing Interval) AND (Long Pacing Interval
<= Maximum Pacing Interval),
        Deliver ATP train;
        F (Pacing Interval - Short Pacing Interval ) < (Long Pacing Interval - Pacing
Interval)
            Set Temporary Pacing Interval = Short Pacing Interval
        ELSE,
            Set Temporary Pacing Interval = Long Pacing Interval
        ENDIF
    ELSEIF (Short Pacing Interval >= Minimum Pacing Interval),
        Deliver ATP Train,
        Temporary Pacing Interval = Short Pacing Interval
    ELSEIF (Long Pacing Interval <= Maximum Pacing Interval)
        Deliver ATP Train,
        Temporary Pacing Interval = Long Pacing Interval
    ELSE
        Wait for the next atrial tachy sense, and repeat the search for a suitable
        Pacing Interval for re-synchronization.
ENDIF
```

Figure 6C:
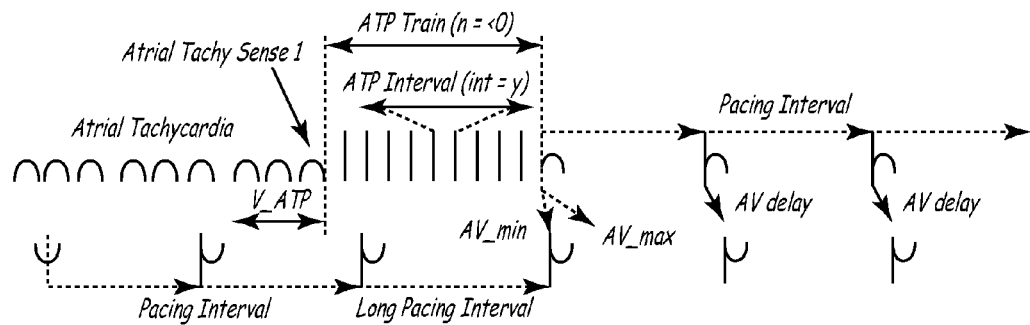
FIG. 6C is a timing diagram illustrating an ATP sequence and ventricular pacing with a lengthened ventricular interval.

Examples of selecting short and long Pacing Intervals are seen in FIGS. 6B and 6C respectively. If both short and long pacing intervals qualify, the one that places the temporary Pacing Interval closest to the initial Pacing Interval is chosen. If only the short Pacing Interval qualifies, it is selected. FIG. 6B illustrates a Short Pacing Interval, where the first ventricular pulse after the end of the train occurs just before the time corresponding to AV_max. In FIG. 6C, the Long Pacing Interval produces a ventricular pace pulse at an AV delay that follows the end of the train by just about AV_min. In both cases, the ventricular pacing Interval then returns to Pacing Interval, and synchronous pacing is continued (assuming a normal sinus rhythm).

Figure 7:
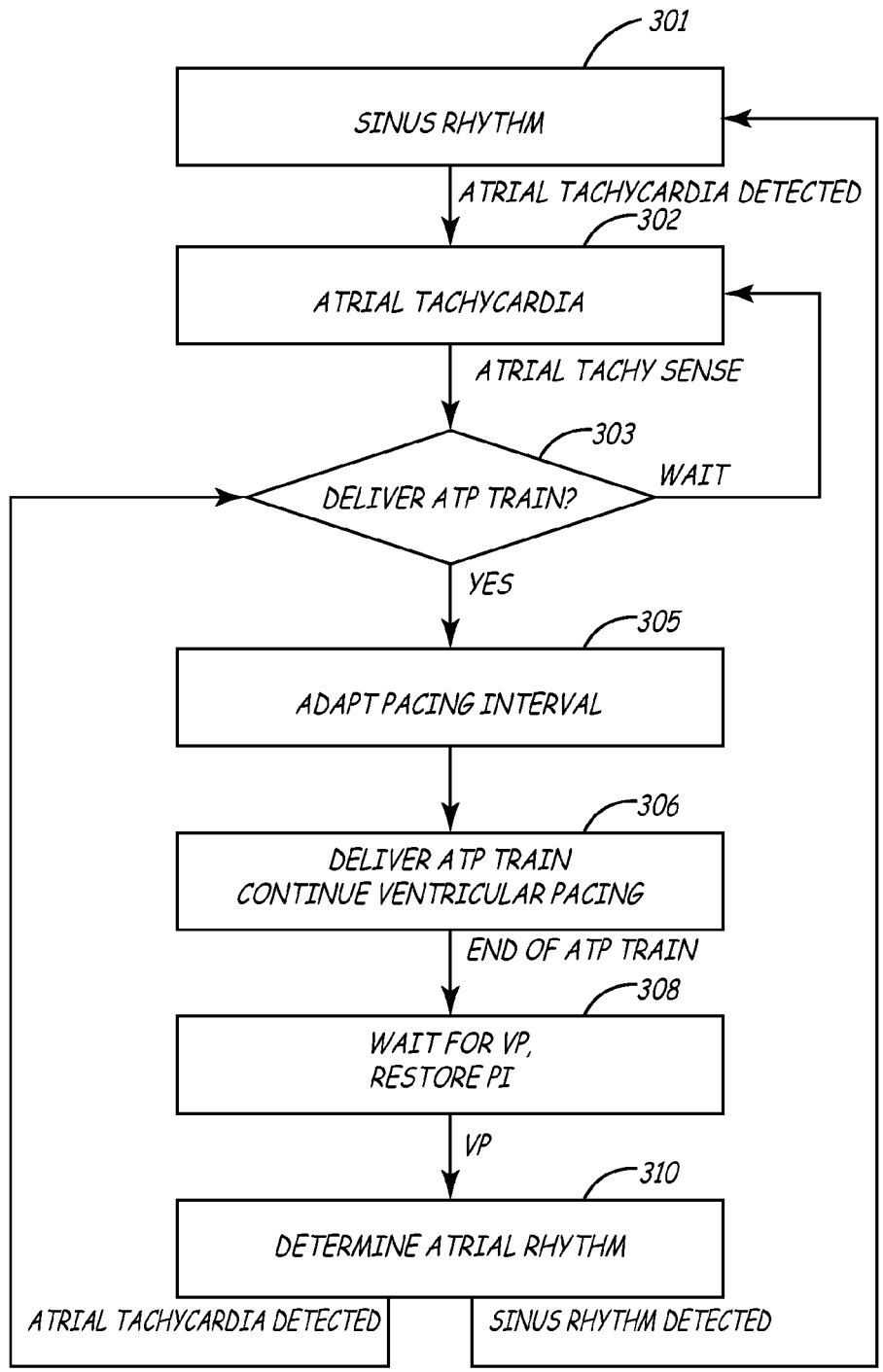
FIG. 7 is a flow diagram showing the primary steps taken by the system of the invention in responding to sensed AT, adapting ventricular pacing interval as necessary, delivering an ATP sequence, pacing the ventricle asynchronously during the ATP sequence and following the sequence with a ventricular pace pulse synchronously timed to the last atrial pulse of the ATP sequence.

FIG. 7 is a flow diagram showing the primary steps taken in carrying out the specific features of this invention. At block 301, the sinus rhythm is examined, by looking at successive intervals between sinus (atrial) beats. The sinus beats, or atrial senses, are determined in a well known manner. An example of an over-all flow diagram for event determination in a dual chamber pacemaker, including determining atrial senses, is presented at FIG. 4, U.S. Pat. No. 6,029, 087, assigned to the assignee of this invention and incorporated herein by reference. See also FIG. 2 of U.S. Pat. No. 6,128,532, also incorporated herein by reference in its entirety. As stated above, in a typical tachy detection scheme, senses are classified as tachy senses if the rate corresponding to the interval is above a predetermined threshold. If such tachy beats are sensed, at block 302 the pacemaker monitors to see if the tachy beats continue for a duration as to constitute AT. If so, AT is determined, and an atrial tachy sense i (as seen in FIGS. 6A–C) signal is sent to block 303. At block 303 the implanted device performs the above logic steps to determine if an ATP train can be delivered along with a Pacing Interval adapted to resynchronize after the train. If not, which is statistically not probable but will occur occasionally, the pacer waits, returning to block 302 where upon the next atrial beat an Atrial Tachy Sense i signal is generated and sent to decision block 303. Upon determining an available temporary Pacing Interval (the current PI, Short PI or Long PI), the Pacing Interval is adapted as shown at block 305. At 306, the ATP train is delivered while ventricular pacing is continued asynchronously. At the end of the ATP train, the pacer waits to deliver the next ventricular pulse, as shown at block 308. After such synchronous delivery, the ventricular pacing interval is restored to Pacing Interval. At 310, the pacer determines whether the atrial rhythm is a normal sinus rhythm or a tachycardia. If a normal sinus rhythm is detected, the pacer goes back to examining the sinus rhythm, as at block 301. However, if the AT has not been interrupted, the pacer returns to decision block 303, and prepares to deliver another ATP train along with an adapted Pacing Interval.

Figure 8:
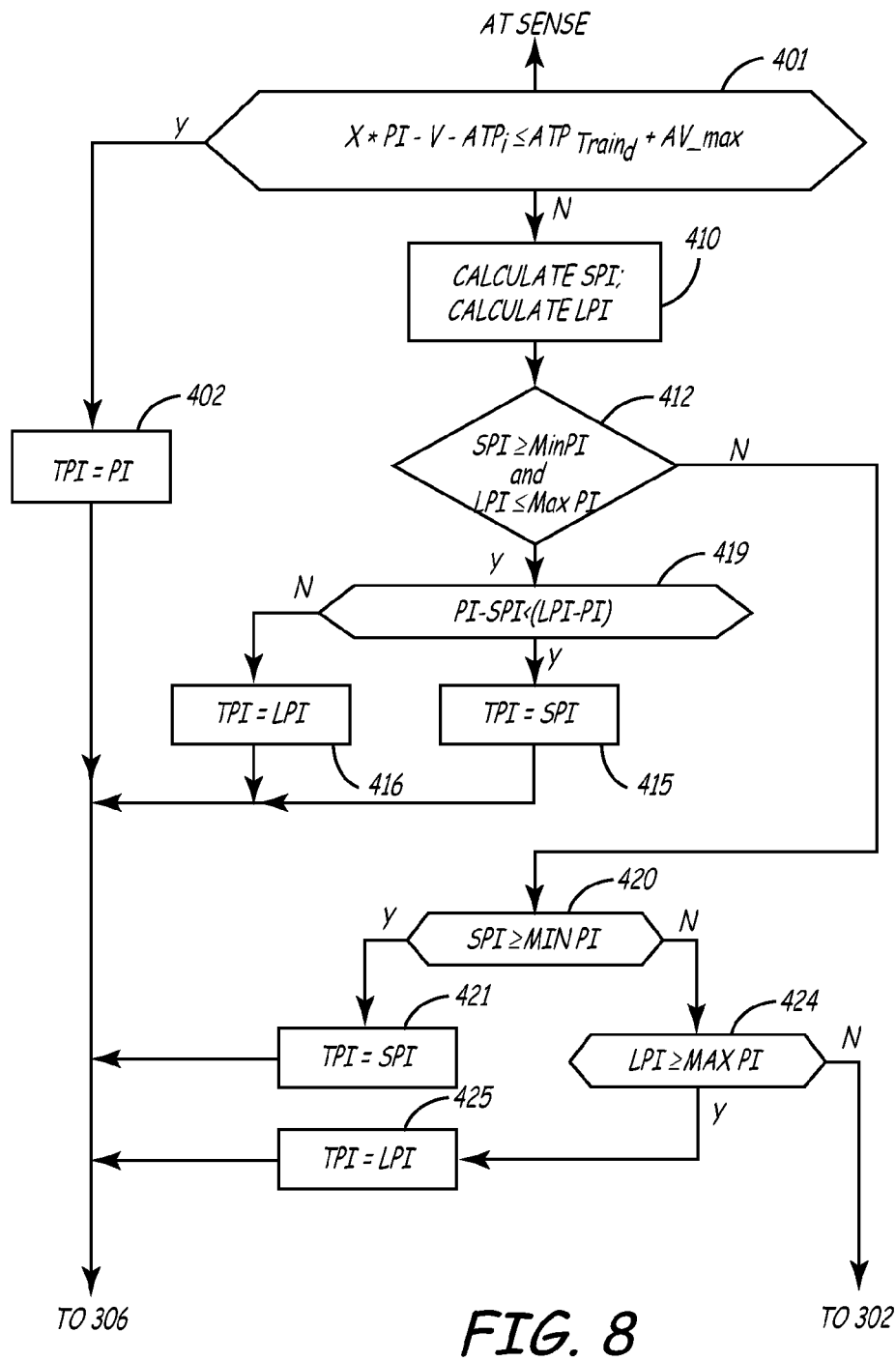
FIG. 8 is a flow diagram illustrating the preferred algorithm for determining the best ventricular pacing interval for use with an ATP sequence.

The logic steps that are carried out at decision block 303 are illustrated in the sub-routine of FIG. 8. At 401, it is determined whether the temporary Pacing Interval (TPI) can be maintained as the current Pacing Interval, by the comparison shown. If yes, at block 402 (part of block 305 in FIG. 7), TPI=PI and the device proceeds to block 306 (FIG. 7) to deliver the ATP train. But if no, then at block 410 the Short Pacing Interval (SPI) and Long Pacing Interval (LPI) are calculated. At 412, it is determined if SPI>=Minimum Pacing Interval AND LPI is<=Maximum Pacing Interval. If yes, at 414 it is determined whether (PI–SPI)<(LPI–PI). If no, TPI is set=LPI at block 416; if yes, then TPI is set=SPI at block 415. Following this, the routine goes to block 306 where the ATP train is delivered.

Returning to block 412, if the answer is NO, the routine goes to block 420 and determines if SPI>=Minimum PI. If YES, TPI is set=SPI at block 421. However, if NO then the routine goes to block 424 and determines if LPI<=Maximum PI. If yes, then TPI is set=LPI at block 425. But if NO, then the train cannot be delivered, and the routine returns to block 302 to wait for the next Atrial Tachy Sense i, after which the sub-routine of FIG. 8 is again entered.

The preferred embodiment of the invention as described meets the objects set forth above, namely to provide re-synchronization of ventricular pacing following delivery of an anti-tachy scheme of atrial pulses designed to interrupt the AT and return the atrium to a normal sinus rhythm. During the ATP sequence, any ventricular pulse that is delivered is an asynchronous pulse at a V—V interval determined by the algorithm. The first ventricular pulse after the end of the train or other ATP scheme follows the last ATP pulse by a delay within the range AV_min to AV_max, and thus is accurately synchronized. It is an important feature of this invention that ventricular pacing is maintained at a rate that meets the criteria that it can't be too slow or too fast. Re-synchronization as such could theoretically be achieved by the simple expedient of timing out a suitable AV delay following the last atrial pulse of the ATP train. However, depending on the timing of the ventricular pace pulses and the duration of the ATP train this would usually result in a V—V interval that was unacceptably short or long. The invention, as seen above, provides for asynchronous pacing at an acceptable rate as well as re-synchronization immediately after the end of the ATP train, thus optimizing conditions for stabilizing the atrium and preventing return of AT or another dangerous atrial arrhythmia. Following re-synchronization, and in the absence of continued AT, the pacing device resumes normal synchronous pacing.

The preceding specific embodiments are illustrative of the practice of the invention. It is to be understood, therefore, that other expedients known to those skilled in the art or disclosed herein, may be employed without departing from the invention or the scope of the appended claims. The present invention is not limited to any particular combination of hardware and software per se, but may find application with any form of software supplementing hardware. Of course, the calculation of a temporary pacing interval is most suitably done with a microprocessor. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable cardiac pacing device, comprising:
   ventricular pacing means for pacing the patient's ventricle with pace pulses at an adaptable pacing interval;
   AT means for determining AT and for determining the timing of the start of an AT episode;
   train means for delivering an ATP train in fixed relation to said AT start;
   algorithm means activated at said start of an AT episode for determining if ventricular pace pulses can be delivered following a said AT start with an adapted pacing interval whereby a synchronized ventricular pace pulse will be delivered synchronized to the last atrial pulse of a said ATP train that has been delivered, said determining including determining said adapted pacing interval subject to predetermined pacing interval and AV criteria;
   temporary means for temporarily changing the pacing interval to said adapted value when it is determined that a said adapted pacing interval can be determined;
   wait means operative if said algorithm means determines that a said synchronized pace pulse cannot be delivered for activating said algorithm means after waiting for sensing of another atrial beat; and
   initiating means for initiating said train means to deliver a said ATP train upon a said pacing interval determination that a synchronized ventricular pace pulse can be delivered.

2. The device as described in claim 1, comprising rhythm means for determining whether AT remains present following delivery of a said ATP train and a said synchronized ventricular pulse.

3. The device as described in claim 1, comprising repeat means for repeating the operation of said algorithm means when AT is determined to be present following delivery of a said ATP train.

4. The device as described in claim 1, comprising storage means for storing criteria relating to maximum and minimum values of pacing interval and maximum and minimum values of AV delay.

5. The device as described in claim 1, comprising revert means operative after delivery of a synchronized pulse for changing said ventricular pacing interval back to the value it had prior to delivery of a said ATP train.

6. The device as described in claim 1, wherein said temporary means controls said ventricular pacing means to deliver ventricular pace pulses asynchronously at said temporary pacing interval during said ATP train duration.

7. The device as described in claim 1, wherein said algorithm means comprises second storage means for storing the duration of said ATP train and means for determining the time interval from the last ventricular pace pulse before AT to the start of said ATP train.

8. The device as described in claim 7, comprising calculation means for calculating when said adapted interval can suitably be the same as the pacing interval before delivery of said ATP train.

9. The device as described in claim 7, wherein said calculation means calculates when said adapted interval can suitably be longer than the pacing interval before delivery of said ATP train.

10. An implantable cardiac pacing system, comprising:
    ventricular pacing means for pacing the patient's ventricle with pace pulses delivered at an adaptable pacing interval;
    AT means for determining the occurrence of AT and for determining a designated time of start of AT;
    train means for delivering an ATP train of atrial pulses in fixed relation to said AT start; and
    adapting means for adapting the pacing interval of said ventricular pacing means so that the next ventricular pace pulse delivered after the end of said ATP train is re-synchronized to the last atrial pulse of said ATP train;
    wherein said adapting means comprises delay means for determining when a suitable pacing interval cannot be calculated at the time of AT start and for then delaying delivery of a said ATP train and calculation of a suitable adapted pacing interval by one atrial cycle.

11. The system as described in claim 10, wherein said train means comprises means for delivering a sequence of atrial pulses at a constant ATP interval and for delivering the first of said train pulses at said ATP interval following said AT start.

12. The system as described in claim 10, wherein said adapting means comprises storage means for storing AV_min and AV_max allowable values of AV delay and sync means for determining a ventricular pacing interval whereby ventricular pace pulses are delivered asynchronously during the duration of said ATP train and the re-synchronized ventricular pace pulse delivered after the conclusion of said ATP train is timed to follow the last atrial pulse of said train by an interval within the range of AV_min to AV_max.

13. The system as described in claim 12, wherein said adapting means comprises algorithm means for determining if the ventricular pacing interval prior to AT start can be maintained and provide for said re-synchronized pulse.

14. The system as described in claim 12, wherein said algorithm means comprises means for determining when the ventricular pacing interval can be set to a shorter value.

15. The system as described in claim 12, wherein said algorithm means comprises means for determining when the ventricular pacing interval can be set to a longer value.

16. The system as described in claim 10, wherein said train means comprises fixed sequence means for delivering a predetermined group of atrial pulses in a fixed sequence, and wherein said adapting means comprises train storage means for storing the duration of said fixed sequence of pulses.

17. The system as described in claim 10, comprising detection means operative following delivery of a said train for detecting if AT remains, and repeat means for repeating the operation of said train means and said adapting means if AT remains.

18. The system as described in claim 17, comprising reset means for resetting the ventricular pacing interval to its former value following delivery of said re-synchronizing pulse.

19. A method of dual chamber pacing, comprising:
  determining the existence of atrial tachycardia (AT) and designating a start of said AT;
  storing data concerning an ATP sequence of atrial pulses to be delivered to interrupt an AT;
  determining a temporary pacing interval for asynchronously pacing the ventricle after start of AT, wherein said temporary pacing interval meets predetermined rate criteria and is calculated to provide for re-synchronization after the last atrial pulse of said ATP sequence;
  delivering said ATP sequence in timed relation to said AT start;
  delivering ventricular pace pulses at said temporary pacing interval through the duration of said sequence;
  delivering the next ventricular pulse following the end of said sequence at said temporary pacing interval, whereby said next ventricular pulse is synchronized to the last atrial pulse of said ATP sequence, thereby re-synchronizing ventricular pacing; and
  determining when a temporary pacing interval cannot be calculated that meets predetermined criteria, delaying delivery of said ATP sequence, and sensing the next atrial beat.

20. The method as described in claim 19, comprising storing the ventricular pacing interval just before AT start, and re-setting said ventricular pacing interval to said stored pacing interval after delivery of said next re-synchronizing pulse.

21. The method as described in claim 19, comprising delivering said sequence of atrial pulses at a constant interval and delivering the first of said sequence of pulses at said constant interval following said AT start.

22. The method as described in claim 19, comprising storing AV_min and AV_max allowable values of AV delay, and wherein said determining comprises determining that said next ventricular pulse is delivered within AV_min to AV_max after said last atrial pulse of said ATP sequence.

23. The method as described in claim 22, comprising storing values of minimum and maximum pacing intervals, and wherein said determining comprises determining that said temporary pacing interval is within the range of AV_min to AV_max.

24. The method as described in claim 19, comprising determining the current pacing interval just before AT start and determining when the temporary pacing interval can be set to a value shorter than said current pacing interval.

25. The method as described in claim 19, comprising determining the current pacing interval just before AT start and determining when the temporary pacing interval can be set to a value equal to said current pacing interval.

26. The method as described in claim 19, comprising determining the current pacing interval just before AT start and determining when the temporary pacing interval can be set to a value longer than said current pacing interval.

27. The method as described in claim 19, comprising detecting if AT remains after delivering a said ATP sequence, and repeating said determining step after sensing said next atrial beat.

28. A pacing system for detecting and treating atrial tachycardia in a patient and re-synchronizing ventricular pacing of the patient directly after the tachycardia treatment, comprising:
  AT means for delivering an ATP train of a fixed sequence of pulses to the patient's atrium;
  temporary means for delivering asynchronous ventricular pacing pulses at a temporary pacing interval to the patient's ventricle during said ATP train and for the next ventricular pacing pulse after the last pulse of said sequence, whereby said next ventricular pacing pulse is synchronously timed with respect to said last sequence pulse, wherein said temporary means comprises calculating means for calculating said temporary pacing interval;
  storage means for storing pacing interval criteria and AV criteria; and
  delay means for delaying the operation of said AT means and said temporary means until said calculating means can calculate a temporary pacing interval that meets said stored pacing interval and AV criteria
  wherein said delay means initiates operation of said AT means and said calculating means after one additional atrial beat is sensed.

29. The system as described in claim 28, wherein said temporary means comprises storage means for storing a range of acceptable AV delay values and said calculating means comprises means for calculating said temporary pacing interval so that said next ventricular pacing pulse is delivered at a delay following said last pulse, where said delay is within said range.

30. The system as described in claim 29, wherein said temporary means comprises limit means for limiting said temporary pacing interval to a value within a predetermined range of pacing intervals.

31. The system as described in claim 28, wherein said calculating means comprises selection means for selecting a pacing interval from among intervals that are longer and shorter than the pacing interval at time of detecting atrial tachycardia.

32. A method of optimising synchronous pacing of a patient following an episode of atrial tachycardia, comprising:
  detecting atrial tachycardia and preparing delivery of an ATP sequence to the patient's atrium;
  calculating a temporary pacing interval for asynchronous pacing of the patient's ventricle while said ATP sequence is delivered and which will enable delivery of a next ventricular pace pulse after the end of said sequence that is synchronously timed in relation to the end of the ATP sequence; and
  delivering said ATP sequence and asynchronously pacing the ventricle at said temporary pacing interval through and including delivery of a synchronous pace pulse to the ventricle after the end of said sequence;

wherein said calculating comprises calculating a pacing interval that is between a predetermined minimum value and a predetermined maximum value and determining that said synchronous pace pulse is delivered within a predetermined AV range following the end of said ATP sequence;

storing values of AV max and AV min; and delivering said synchronous pace pulse at an AV delay after the end of said ATP sequence that is no less than AV min and no more than AV max.

33. The method as described in claim 32, comprising storing a current pacing interval before detection of atrial tachycardia and resuming synchronous pacing with said current pacing interval after delivery of said synchronous pace pulse.

34. The method as described in claim 32 comprising defining the start of atrial tachycardia, and delivering said ATP sequence and said asynchronous pulses in timed relation to said start.

35. The method as described in claim 34, comprising determining if a suitable temporary pacing interval can be used, and if not waiting for a next atrial beat and then calculating said temporary pacing interval.

36. A system of cardiac pacing of a patient, comprising:

AT means for detecting the presence of AT;

ATP means for delivering an ATP sequence of atrial pulses to the patient's atrium in response to detected AT;

ventricular pacing means for pacing the patient's ventricle;

rate criteria means for limiting the rate of ventricular pacing; and control means for controlling said ventricular pacing means to deliver ventricular pace pulses during said ATP sequence and for a next ventricular pace pulse after the end of said sequence at a rate that meets said rate criteria and provides that said next ventricular pace pulse is in cardiac synchrony with the last atrial pulse of said sequence wherein said control means comprises AV means for storing predetermined AV criteria including values of AV max and AV min and calculating means for calculating a temporary pacing interval that meets said rate criteria and said AV criteria and also provides that said next ventricular pace pulse is delivered following said last atrial pace pulse by an AV interval that is no less than AV min and no more than AV max.

* * * * *